United States Patent
Ettl et al.

Patent Number: 5,672,721
Date of Patent: Sep. 30, 1997

[54] PREPARATION OF LOW-SOLVENT ALKYL DIKETENES

[75] Inventors: Roland Ettl, Hassloch; Wolfgang Kasel, Nussloch; Matthias Fankhänel, Ludwigshafen; Wolfgang Reuther, Heidelberg, all of Germany

[73] Assignee: BASF Aktiengesellschaft, Ludwigshafen, Germany

[21] Appl. No.: 638,225

[22] Filed: Apr. 26, 1996

[30] Foreign Application Priority Data

May 3, 1995 [DE] Germany .................. 195 16 183.1

[51] Int. Cl.$^6$ .................................. C07D 305/12
[52] U.S. Cl. ......................................... 549/329
[58] Field of Search ............................... 549/329

[56] References Cited

U.S. PATENT DOCUMENTS

| | | |
|---|---|---|
| 5,399,774 | 3/1995 | McIntosh et al. ............ 568/301 |
| 5,484,952 | 1/1996 | Nolan et al. ................. 549/329 |
| 5,502,218 | 3/1996 | Nicholass et al. ........... 549/329 |
| 5,525,738 | 6/1996 | Zhang ........................... 549/329 |

FOREIGN PATENT DOCUMENTS

| | | |
|---|---|---|
| 0 550 107 A1 | 7/1993 | European Pat. Off. . |
| 23 27 988 A1 | 6/1973 | Germany . |
| 29 27 118 A1 | 7/1979 | Germany . |
| WO94/18389 | 8/1994 | WIPO . |

*Primary Examiner*—Mukund J. Shah
*Assistant Examiner*—Deepak R. Rao
*Attorney, Agent, or Firm*—John H. Shurtleff

[57] ABSTRACT

A process for the preparation of low-solvent alkyl diketenes of the general formula:

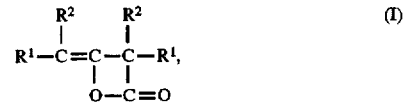

in which $R^1$ denotes $C_{10}$–$C_{30}$ alkyl or $C_{10}$–$C_{30}$ alkenyl and
$R^2$ denotes hydrogen or $C_1$–$C_8$ alkyl, by causing carboxylic chlorides of the formula II

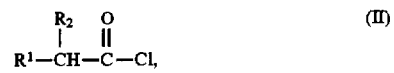

in which $R^1$ and $R^2$ have the aforementioned meanings, to react with tertiary amines of the formula III

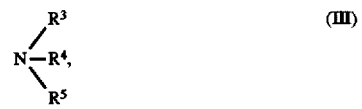

in which $R^3$, $R^4$, $R^5$ denote $C_1$–$C_{12}$ alkyl or $C_3$–$C_{12}$ cycloalkyl and
$R^3$ and $R^4$ together denote a $C_2$–$C_{11}$ alkylene dichain optionally interrupted by oxygen or nitrogen, in a substantially water-immiscible, inert solvent, wherein distillation is carried out at temperatures ranging from 80° to 130° C. and pressures ranging from 10 to 500 mbar and subsequently with the addition of water or steam.

14 Claims, No Drawings

PREPARATION OF LOW-SOLVENT ALKYL DIKETENES

The present invention relates to a process for the preparation of low-solvent alkyl diketenes formed by causing carboxylic chlorides to react with tertiary amines in substantially water-immiscible, inert solvent, by distillation initially without, and then with, water or steam.

Alkyl diketenes (AKD) are used predominantly as water-repellent agents in the paper-manufacturing industry. To this end alkyl diketenes, a waxy, water-insoluble substance, are usually added to a dispersion using ionically modified starch or synthetic polymers (anionic or cationic) as protective colloids.

DE-A 2,327,988 reveals the preparation of alkyl diketenes by causing fatty acid chlorides to react with tertiary amines, preferably triethylamine, in anhydrous solvents, for example toluene, followed by extraction of the amine hydrochloride with a neutral salt solution of low concentration.

DE-A 2,927,118 reveals the preparation of alkyl diketenes by causing fatty acid chlorides to react with tertiary amines, preferably a mixture of dimethylcyclohexylamine and trimethylamine, in anhydrous solvents, for example toluene. In addition to the complicated and elaborate handling of two different tertiary amines the purification and quantitative recycling Of the two amines presents its problems.

In both cases the alkyl diketenes obtained still contain, following isolation, by distillation, considerable residual amounts of solvent (ca 1%). A reduction thereof can be achieved only by the employment of very extensive process engineering measures (high vacuum, high temperatures). On the other hand, however, there is a lack of thermostability (decomposition to polymeric products).

EP-A 550,107 reveals a process, in which carboxylic chlorides are caused to react with tertiary amines in the absence of solvents. The reaction equipment mentioned as being suitable for this purpose is very elaborate for industrial applications and can only be used for this process. Moreover the purification is found to be time consuming. In the aqueous extraction of the amine hydrochloride the phase separation is sluggish due to the high viscosity of the organic phase (=alkyl diketenes). In the case of incomplete conversion to alkyl diketenes moreover very stable emulsions are formed which lead to a low yield and thus make the process less economical.

WO-A 94/18389 reveals a process, in which residues of organic solvents are removed by the addition of adsorbents. To this end aqueous dispersions of alkyl diketenes are first prepared and then mixed with suitable adsorbents, for example zeolites, which take up the organic solvent. This process is complicated, since the adsorbents added must again be removed by filtration following the take-up of the organic solvent.

It is thus an object of the present invention to overcome the above drawbacks.

Accordingly, we have found a novel and improved process for the preparation of low-solvent alkyl diketenes of the formula I

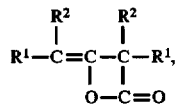

in which $R^1$ denotes $C_{10}$–$C_{30}$ alkyl or $C_{10}$–$C_{30}$ alkenyl and $R^2$ denotes hydrogen or $C_1$–$C_8$ alkyl, by causing carboxylic chlorides of the formula II

in which $R^1$ and $R^2$ have the aforementioned meanings, to react with tertiary amines of the formula III

in which $R^3$, $R^4$, $R^5$ denote $C_1$–$C_{12}$ alkyl or $C_3$–$C_{12}$ cycloalkyl and $R^3$ and $R^4$ together denote a $C_2$–$C_{11}$ alkylene dichain optionally interrupted by oxygen or nitrogen, in a substantially water-immiscible, inert solvent, wherein distillation is carried out at temperatures ranging from 80° to 130° C. and pressures ranging from 10 to 500 mbar and subsequently with the addition of water or steam.

The process of the invention can be carried out as follows:

A carboxylic chloride II can be caused to react with a tertiary amine III in a substantially water-immiscible inert organic solvent, preferably substantially anhydrous inert organic solvent and more preferably in an anhydrous inert organic solvent at temperatures ranging from 40° to 95° C. and preferably from 50° to 80° C. and more preferably 60° to 65° C. under pressures ranging from 0.1 to 3 bar, preferably from 0.5 to 1.5 bar and more preferably under standard pressure conditions (atmospheric pressure) and the solvent then removed, following aqueous extraction of the organic phase, by distillation under a pressure of from 10 to 500 mbar, preferably 30 to 350 mbar and more preferably 50 to 250 mbar and temperatures ranging from 80° to 130° C., preferably 95° to 120° C. and more preferably 100° to 115° C.. Afterwards steam or water can be metered into the reaction boiler under a pressure of from 10 to 500 mbar, preferably 30 to 350 mbar and more preferably 50 to 250 mbar and temperatures ranging from 80° to 130° C., preferably 95° to 120° C. and more preferably 100° to 115° C.

Metering of steam is preferably usually carried out directly into the alkyldiketene/toluene solution. Metering of water is carried out either upwardly or downwardly into the alkyldiketene-toluene solution or downwardly onto the surface of the alkyldiketene-toluene solution. Metering may be simply effected via an inlet tube, preferably in the proximity of the stirrer, or alternatively via more elaborate constructions (perforated annular pipes, etc).

The azeotrope comprising water and organic solvent is usually condensed and separated into an aqueous phase (possibly contaminated with traces of solvent) and an organic phase. Both phases can be reused in the next reaction batch.

Following the metered introduction of the desired amount of water or steam distillation is usually continued for a while (ca 10 to 45 min under a vacuum of from 10 to 50 mbar at 100° to 120° C.). The reaction vessel is then usually purged with nitrogen and cooled.

The toluene content in the alkyldiketene can be determined by the usual analytical methods (for example GC). Suitable substantially water-immiscible, inert solvents are alkanes, for example $C_5$–$C_{30}$ alkanes such as n-pentane, isopentane, pentane mixtures, n-hexane, isohexane, hexane mixtures, n-heptane, n-octane, preferably n-hexane, isohexane, hexane mixtures, n-heptane mixtures, n-octane mixtures, more preferably hexane mixtures, cycloalkanes, for example $C_5$–$C_2$ cycloalkanes such as cyclopentane, cyclohexane, cycloheptane, cyclooctane, methylcyclohexane, ethylcyclohexane, preferably cyclohexane and methylcyclohexane, more preferably cyclohexane, aromatic hydrocarbons such as benzene, toluene, xylenes, preferably benzene and toluene, more preferably toluene, chlorinated alkanes for example 1,2-dichloro-propane, 1,2-dichlorobutane, preferably 1,2-dichloropropane, ethers, for example diethylether, diisopropylether, diisoamylether, di-n-hexylether, methyl-tert-butyl-ether, preferably diisopropylether and methyl-tert-butylether or mixtures thereof.

The molar ratio of amine III to carboxylic chloride II is usually 0.1:1 to 30:1, preferably 1:1 to 3:1, more preferably 1:1 to 1.2:1.

The ratio by weight of inert solvent to carboxylic chloride II is usually 0.01:1 to 100:1, preferably 0.5:1 to 2:1, more preferably 0.8:1 to 1:1.

The amount of water or steam required is usually 3 to 300 wt %, preferably 5 to 50 wt %, more preferably 5 to 30 wt % based on the alkyldiketene I.

The carboxylic chlorides I are usually longer-chain saturated or unsaturated acid chlorides containing 12 or more carbon atoms, preferably containing 16 or more carbon atoms; also mixtures of acid chlorides derived from natural fatty acids may be used such as the fatty acids derived from coconut oil, tall oil, castor oil, olive oil, beef tallow, palm nut oil, it is preferred to use fatty acid mixtures containing $C_{16}$–$C_{22}$, more preferably $C_{16}$–$C_{18}$.

The substituents $R^1$, $R^2$, $R^3$, $R^4$ and $R^5$ in the compounds I, II and III have the following meanings:

$R^1$ $C_{10}$–$C_{30}$ alkyl, preferably $C_{12}$–$C_{25}$ alkyl, more preferably $C_{12}$–$C_{20}$ alkyl such as dodecyl, tetradecyl and hexadecyl, $C_{10}$–$C_{30}$ alkenyl, preferably $C_{12}$–$C_{25}$ alkenyl, more preferably $C_{12}$–$C_{20}$ alkenyl such as tetradec-7-1-yl and hexadec-7-1-yl, $R^2$ hydrogen, $C_1$–$C_8$ alkyl, preferably $C_1$–$C_4$ alkyl such as methyl, ethyl, n-propyl, isopropyl, n-butyl, isobutyl, sec-butyl, tert-butyl, more preferably methyl and ethyl, $R^3$, $R^4$, $R^5$ $C_1$–$C_{12}$ alkyl, preferably $C_1$–$C_8$ alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl and isododecyl, more preferably $C_1$–$C_4$ alkyl such as methyl, ethyl, n-propyl, isopropyl, n-butyl, isobutyl, sec-butyl and tert-butyl, $C_3$–$C_{12}$ cycloalkyl, preferably $C_3$–$C_8$ cycloalkyl such as cyclopropyl, cyclobutyl, cyclopentyl, cyclohexyl, cycloheptyl and cyclooctyl, more preferably cyclopentyl, cyclohexyl and cyclooctyl, $R^3$, $R^4$ together a $C_2$–$C_{11}$ alkylene dichain optionally interrupted by oxygen or nitrogen, preferably a $C_3$–$C_7$ alkylene dichain optionally interrupted by oxygen or nitrogen, such as —(CH$_2$)$_3$—, —(CH$_2$)$_4$—, —(CH)$_2$—, —(CH$_2$)$_5$—, —(CH$_2$)$_2$—N—(CH$_2$)$_2$— and —(CH$_2$)$_2$—O—(CH$_2$)$_2$—.

The "solvent-free" AKD is used for hydrophobizing paper; AKD having a low solvent content has an advantageous influence on keeping properties (toluene has a negative influence on the shelf life), on its use in paper mills (the solvent escapes in the drying section of paper mills) and on the subsequent use of the resulting papers (for example in the manufacture of cartons for drinks (Tetrapak) where no solvents are tolerated due to the contact with food).

The process of the invention can also be applied to other organic substances, which mainly react with water on account of their structure, are present in solution in an organic solvent, and are to be purified by distillation and when there is the necessity for a low solvent content: for example anhydrides, imides of long-chain fatty acids, mixed anhydrides or imides of long-chain fatty acids with other carboxylic acids/carboxylic derivatives, for example acylated caprolactams and acylated benzoic acids.

EXAMPLE 1

To 230 g of dimethylcyclohexylamine in 400 g toluene there were metered 480 g of stearic chloride at a temperature of 60° C. and stirring was continued for 1 h. The mixture was then acidified with sulfuric acid and extracted twice with water. The major portion of the solvent of the organic phase was distilled off at temperatures ranging from 100° to 110° C. in vacuo (100 mbar) and then a total of 240 g of steam were introduced whilst maintaining the temperature and vacuum. Distillation was continued for a further 30 min before the reaction vessel was purged with nitrogen and cooled. The yield was 97.3% with an alkyldiketene content of 92.6%.

EXAMPLE 2

To 160 g of triethylamine in 520 g of toluene there were metered 445 g of stearic chloride at a temperature of 65° C. and stirring was continued for 1 h. The mixture was then acidified with sulfuric acid and extracted twice with water. The major portion of the solvent of the organic phase was distilled off at temperatures ranging from 100° to 110° C. in vacuo (145 mbar) and then a total of 120 g of steam were introduced whilst maintaining the temperature and vacuum conditions. Distillation was continued for a further 30 min, before the reaction vessel was purged with nitrogen and cooled. The yield was 97.3% with an alkyldiketene content of 92.6%.

EXAMPLE 3

To 214 g of triethylamine in 530 g of toluene there were metered 560 g of stearic chloride at a temperature of 65° C. and stirring was continued for 1 h. The mixture was then acidified with sulfuric acid and extracted twice with water. The major portion of the solvent of the organic phase was distilled off at temperatures ranging from 100° to 110° C. in vacuo (70 mbar) and then a total of 180 g of water were metered in whilst maintaining the temperature and vacuum conditions. Distillation was continued for a further 30 min before the reaction vessel was purged with nitrogen and cooled. The yield was 99.1% with an alkyldiketene content of 91.5%.

Toluene content of the alkyl diketenes prepared (determined by GC analysis):

| Example No. | Toluene content [ppm] |
|---|---|
| 1 | <2 |
| 2 | 5 |
| 3 | 8 |
| Comparative Example A | 7350 |

COMPARATIVE EXAMPLE A

Comparative Example A (carried out in accordance with DE-A 2,927,118 Example No. 4)

To 245 g of dimethylcyclohexylamine in 500 g of toluene there were metered 500 g of stearic chloride at a temperature of 60° C. and stirring was continued for 1 h. The mixture was then acidified with sulfuric acid and extracted twice with water and the organic phase was freed from toluene by distillation (distillation: 100° to 110° C., 15 mbar). The yield was 97% with an alkyldiketene content of 86.7%.

We claim:

1. A process for the preparation of low-solvent alkyl diketenes of the general formula:

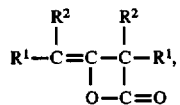

in which $R^1$ denotes $C_{10}$–$C_{30}$ alkyl or $C_{10}$–$C_{30}$ alkenyl and $R^2$ denotes hydrogen or $C_1$–$C_8$ alkyl, by causing carboxylic chlorides of the formula II

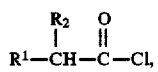

in which $R^1$ and $R^2$ have the aforementioned meanings, to react with tertiary amines of the formula III

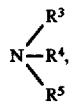

in which $R^3$, $R^4$, $R^5$ denote $C_1$–$C_{12}$ alkyl or $C_3$–$C_{12}$ cycloalkyl and $R^3$ and $R^4$ together denote a $C_2$–$C_{11}$ alkylene dichain optionally interrupted by oxygen or nitrogen, in a substantially water-immiscible, inert solvent, wherein distillation is carried out in two stages, first at temperatures ranging from 80° to 130° C. and pressures ranging from 10 to 500 mbar and subsequently with the addition of water or steam.

2. A process for the preparation of low-solvent alkyl diketenes I as defined in claim 1, wherein $R^1$ denotes $C_{12}$–$C_{25}$ alkyl or $C_{12}$–$C_{25}$ alkenyl.

3. A process for the preparation of low-solvent alkyl diketenes I as defined in claim 1, wherein $R^1$ denotes $C_{14}$–$C_{20}$ alkyl or $C_{14}$–$C_{20}$ alkenyl.

4. A process for the preparation of low-solvent alkyl diketenes I as defined in claim 1, wherein the distillation is carried out at temperatures ranging from 95° to 120° C. and pressures ranging from 30 to 350 mbar.

5. A process for the preparation of low-solvent alkyl diketenes I as defined in claim 1, wherein the distillation is carried out at temperatures ranging from 100° to 115° C. and pressures ranging from 50 to 250 mbar.

6. A process as claimed in claim 3, wherein $R^2$ in formula I represents hydrogen.

7. A process as claimed in claim 1, wherein $R^2$ in formula I represents hydrogen.

8. A process as claimed in claim 2, wherein $R^2$ in formula I represents hydrogen.

9. A process as claimed in claim 1, wherein the initial reaction of a carboxylic chloride II with said tertiary amine III is carried out in said anhydrous water-immiscible organic solvent at a temperature of from 40° to 95° C. and under a pressure of from 0.1 to 3 bar, the organic phase containing the initial alkyl diketene product being extracted with water and then being subjected to distillation in two stages, first without adding water or steam at a temperature of 80° to 130° C. and under a reduced pressure of from 10 to 500 mbar and subsequently by the addition of water or steam with azeotropic distillation in the same range of temperature and reduced pressure to complete the substantial removal of the organic solvent.

10. A process as claimed in claim 9, wherein the azeotropic distillation in the second stage is sufficient to reduce the content of the organic solvent in the alkyl diketene product to less than 100 ppm.

11. A process as claimed in claim 9, wherein the azeotropic distillation in the second stage is sufficient to reduce the content of the organic solvent in the alkyl diketene product to less than 10 ppm.

12. A process as claimed in claim 9, wherein the amount of water or steam added in the second distillation stage is from 3 to 300% by weight based on the alkyl diketene I.

13. A process as claimed in claim 9, wherein the amount of water or steam added in the second distillation stage is from 5 to 50% by weight based on the alkyl diketene I.

14. A process as claimed in claim 9, wherein the amount of water or steam added in the second distillation stage is from 5 to 30% by weight based on the alkyl diketene I.

* * * * *